United States Patent [19]

Fukuda et al.

[11] Patent Number: 5,373,052
[45] Date of Patent: Dec. 13, 1994

[54] ORGANIC POLYMER MICROPARTICLE AND PROCESS FOR PRODUCING THE SAME

[75] Inventors: Koichi Fukuda, Suita; Hisaki Tanabe, Yawata; Yoshio Eguchi, Ikeda, all of Japan

[73] Assignee: Nippon Paint Co., Ltd., Osaka, Japan

[21] Appl. No.: 992,749

[22] Filed: Dec. 18, 1992

[30] Foreign Application Priority Data

Dec. 20, 1991 [JP] Japan ................... 3-338403

[51] Int. Cl.$^5$ .................... C08G 63/91; C08H 1/00; C08H 5/00; C08L 89/00
[52] U.S. Cl. .................... 525/54.1; 525/54.3; 525/54.31; 526/238.1; 526/238.21; 526/238.22; 526/238.23
[58] Field of Search .................... 525/54.1, 54.3, 54.31; 526/238.1, 238.2, 238.21, 238.22, 238.23

[56] References Cited

U.S. PATENT DOCUMENTS

| | | | |
|---|---|---|---|
| 4,079,025 | 3/1978 | Young et al. | 526/238.22 |
| 4,504,641 | 3/1985 | Nochumson | 526/238.23 |
| 4,572,638 | 6/1988 | Nowinski et al. | 526/238.1 |

FOREIGN PATENT DOCUMENTS 60-90243  5/1985  Japan.

*Primary Examiner*—Nathan M. Nutter
*Attorney, Agent, or Firm*—Townsend & Banta

[57] ABSTRACT

Disclosed is an organic polymer microparticle which is obtainable from copolymerization of (a) an ethylenically unsaturated amine polymer obtained by reacting an amine polymer having at least two primary amino groups with 0.01 to 0.99 molar equivalents based on the amount of the primary amino group, of an unsaturation introducing monomer having at least one functional group which is reactive with the primary amino group and an ethylenic double bond with (b) 10 to 99000 parts by weight based on the total amount (100 parts by weight) of the amine polymer and the unsaturation introducing monomer, of a matrix forming ethylenically unsaturated monomer, in an aqueous medium. A process for producing the organic polymer microparticle is also disclosed.

5 Claims, No Drawings

ORGANIC POLYMER MICROPARTICLE AND PROCESS FOR PRODUCING THE SAME

FIELD OF THE INVENTION

The present invention relates to an organic polymer particle and a process for producing the same. Particularly, it relates to an organic polymer microparticle containing a primary or secondary amino group, which can be used as diagnostic drugs, pharmaceutical carriers, chromatographic carriers, viscosity modifiers, resin molding materials, crosslinking agents, curing agents and cosmetic additives, and a process for producing the same.

DEFINITION OF TERMS IN THE SPECIFICATION

The term "unsaturation introducing monomer" means a monomer having at least one functional group which is reactive with a primary amino group in an amine polymer, and ethylenic double bond. The resulting amine polymer into which ethylenically unsaturated groups are introduced is referred to as an "ethylenically unsaturated amine polymer".

The term "matrix forming ethylenically unsaturated monomer" means an ethylenically unsaturated monomer normally used for forming a resin particle matrix, which is liquid or solid under room temperature.

BACKGROUND OF THE INVENTION

Functional polymers such as ion exchange resin, chelete resin and the like have been widely used as carriers for various chemical substances, heretofore. These functional polymers generally have various reactive groups (for example, active hydrogen-containing groups, such as carboxyl groups, hydroxyl groups and primary or secondary amino groups) on their surface.

Recently, it has been also proposed to fix a biologically active substance (e.g. drug, enzyme, etc.) to the functional polymer to convey it to a focus. In such the application, it is necessary that a functional polymer carrier carries a predetermined amount of drugs, uniformly and securely. Further, it is also necessary that the functional polymer has good dispersibility to various solvents. In general, when the functional polymer is used as a carrier for drugs, it is preferred to use those having primary or secondary amino groups which have a variety of reactivity to form a stable bond with various functional groups.

Accordingly, in order to securely carry the drug, it is preferred that the functional polymer has primary or secondary amino groups. Further, it is possible to control an amount of the drug to be carried and dispersibility to various solvents by changing a particle size of the functional polymer to modify a surface area of the polymer. However, in order to obtain good solvent dispersibility, the particle size of the functional microparticle must be uniformly adjusted to about $10\mu$ or less.

The uniform functional polymer microparticle having good carrying property can also be used as chromatographic carriers, viscosity modifiers, resin molding materials, paint additives, crosslinking agents, curing agents and cosmetic additives, in addition to the application as the above pharmaceutical carriers and, therefore, demand for the polymer is increasing.

The organic polymer particles having primary or secondary amino groups are known. For example, in Japanese Patent Kokai No. 60-90243, there is described a process for producing particles by internally crosslinking an aqueous polyallylamine solution. However, in this process, it is difficult to control a particle size of the particle to be obtained and no particle having a particle size of about no more than $10\mu$ can be obtained.

OBJECTS OF THE INVENTION

One object of the present invention is to provide an organic polymer microparticle having an average particle size of about no more than $10\mu$, which can be suitably used for the application such as diagnostic drugs, pharmaceutical carriers, chromatographic carriers, viscosity modifiers, resin molding materials, paint additives, crosslinking agents, curing agents and cosmetic additives.

Another object of the present invention is to provide a process for producing the organic polymer microparticle.

These objects as well as other objects and advantages of the present invention will become apparent to those skilled in the art from the following description.

SUMMARY OF THE INVENTION

According to the present invention, there is provided an organic polymer microparticle which is obtained by copolymerizing in an aqueous medium;

(a) an ethylenically unsaturated amine polymer having an ethylenic double bond, obtained by reacting an amine polymer having at least two primary amino groups with 0.01 to 0.99 molar equivalents based on the amount of the primary amino group, of an unsaturation introducing monomer having at least one functional group which is reactive with the primary amino group and an ethylenic double bond, with (b) a matrix forming ethylenically unsaturated monomer; an amount of the matrix forming ethylenic unsaturated monomer being 10 to 99,000 parts by weight based on 100 parts by weight of the total amount of said amine polymer and said unsaturation introducing monomer (m).

The organic polymer microparticle of the present invention is made by a process for producing an organic polymer microparticle comprising:

(i) a step of reacting an amine polymer having at least two primary amino groups with 0.01 to 0.99 molar equivalents based on the amount of the primary amino group, of an unsaturation introducing monomer having at least one functional group which is reactive with the primary amino group and an ethylenic double bond to obtain a reaction mixture containing an ethylenically unsaturated amine polymer having an ethylenic double bond, and (ii) a step of formulating 10 to 99000 parts by weight based on 100 parts by weight of the total amount of the amine polymer and the unsaturation introducing monomer, of a matrix forming ethylenically unsaturated monomer in the reaction mixture to copolymerize the ethylenically unsaturated amine polymer with the matrix forming ethylenically unsaturated monomer in an aqueous medium.

DETAILED DESCRIPTION OF THE INVENTION

The amine polymer which can be used in the present invention is a polymer having at least two primary amino groups. Preferably, it is an organic or inorganic solvent-soluble or dispersible polymer having a molecular weight of 60 to 50,000 and an amine equivalent of 1 to 35 mmoles/g, more preferably a molecular weight of 116 to 10,000 and an amine equivalent of 2 to 24 mmoles/g.

Preferred examples of the amine polymer to be used in the present invention include polyamino acids (e.g. polylysine and derivative thereof, gelatin, etc.), polysaccharides (e.g. chitosan and chitosan derivative, etc.) polyamine-vinyl polymer (e.g. polyvinylamine and polyallylamine, etc.), organic silicone polymers (e.g. amine-modified organic silicone oil, etc.) and the like. Particularly, polylysine, polyallyamine, polyvinylamine, amine-modified organic silicone oil and derivative thereof are preferable as the amine polymer.

In the present invention, ethylenically unsaturated groups are introduced into the amine polymer by reacting the amine polymer with the unsaturation introducing monomer. Examples of the preferred unsaturation introducing monomer to be used in the present invention include glycidyl group-containing ethylenically unsaturated monomers which can be subjected to addition reaction with an amino group (e.g. glycidyl methacrylate, alicyclic epoxy methacrylate, allylglycidyl ether, etc.), acryloyl group-containing ethylenically unsaturated monomers which can be subjected to Michael addition reaction with an amino group (e.g. methacryloyloxyethyl acrylate, etc.), isocyanate ethylenically unsaturated monomers which can be subjected to addition reaction with an amino group (e.g. isocyanate ethyl methacrylate, methacrylamide isocyanate, etc.), carboxyl group-containing ethylenically unsaturated monomers which can be subjected to condensation reaction with an amino group (e.g. methacrylic acid, etc.), methacrylates which can be subjected to condensation reaction with an amino group (e.g. methyl methacrylate, etc.), aldehyde ethylenically unsaturated monomers which can be subjected to condensation reaction with an amino group (e.g. methacrolein, etc.), vinyl group-containing vinylbenzyl chlorides which can alkylate an amino group (e.g. vinylbenzyl chloride), vinyl group-containing organic chloride compounds (e.g. methacryl chloride, etc.), and acid anhydrides which can be subjected to addition reaction with an amino group (e.g. maleic anhydride, itaconic anhydride etc.).

Particularly, aliphatic and alicyclic epoxy ethylenically unsaturated monomers such as glycidyl methacrylate, 3,4-epoxycyclohexylmethyl methacrylate [commercially available from Daicel Chemical Industries Co. under the trade name of "Cyclomer M-100"], allylglycidyl ether and vinylcyclohexene monoepoxide [commercially available from Daicel Chemical Industries Co. under the trade name of "Celloxide 2000"] are preferable as the unsaturation introducing monomer to be used in the present invention.

The unsaturation introducing monomer is used in an amount of 0.01 to 0.99 molar equivalents, preferably 0.10 to 0.50 molar equivalents, based on the amount of the primary amino group contained in the amine polymer. When the amount of the unsaturation introducing monomer is less than 0.01 molar equivalent, an introduction rate of ethylenic unsaturation is too small and copolymerizability of the matrix forming ethylenically unsaturated monomer to the amine polymer is lowered, which results in deterioration of quality of the resulting microparticle. When the amount of the unsaturation introducing monomer exceeds 0.99 molar equivalent, the amount of the amino group which is introduced into the microparticle is too small and, therefore, carrying property of the resulting microparticle is lowered.

In the present invention, the resulting ethylenically unsaturated amine polymer is then copolymerized with the matrix forming ethylenically unsaturated monomer. Preferably, the matrix forming ethylenically unsaturated monomer may be selected from the group consisting of methacrylate, methacrylamide and derivative thereof, vinyl monomer, vinyl ether monomer and vinyl ester monomer, which have no high reactivity with primary or secondary amino groups.

Typical examples of the matrix forming ethylenically unsaturated monomer include vinyl ester monomers (e.g. vinyl acetate, vinyl propionate, vinyl butyrate, etc.); aromatic vinyl monomers (e.g. styrene, chlorostyrene, α-methylstyrene, vinyltoluene, vinylnaphthalene, etc.); heterocyclic vinyl monomers (e.g. vinyl oxazoline, vinylpyrrolidone, vinylfuran, vinylpyridine, etc.); vinyl ether monomers (e.g. methyl vinyl ether, isopropyl vinyl ether, n-butyl vinyl ether, isobutyl vinyl ether, etc.); alkyl methacrylates having an alkyl ester portion of 1 to 18 carbon atoms and aromatic derivatives thereof; reaction products of methacrylic acid with butyl, phenyl or glycidyl ether; hydroxymethacrylates (e.g. hydroxyethyl methacrylate, hydroxypropyl methacrylate, etc.), basic methacruylates (e.g. hydroxyethylamino methacrylate, hydroxypropylamino methacrylate, etc.); methacrylamides (e.g. methacrylamide, N-methylmethacrylamide, N-dimethylaminopropylmethacrylamide, N-methylolmethacrylamide, etc.) and derivatives thereof; methacrylonitrile and the like. Particularly, methacrylate derivatives (e.g. methyl methacrylate, n-propyl methacrylate, ethylhexyl methacrylate, etc.); vinyl monomers (e.g. styrene, vinylpyridine, etc.); methacrylamides (e.g. methacrylamide, N-methylmethacrylamide, etc.) and derivatives thereof; methacrylonitriles; vinyl esters (e.g. vinyl acetate, etc.) are preferable as the matrix forming ethylenically unsaturated monomer to be used in the present invention.

For the purpose of improving internal crosslinking property of the microparticle, polyfunctional ethylenically unsaturated monomers such as divinylbenzene, ethylene glycol dimethacrylate or neopentyl glycol dimethacrylate can be optionally used.

It is preferable that the matrix forming ethylenically unsaturated monomer is used in an amount of 10 to 99,000 parts by weight, particularly 50 to 10,000 parts by weight, based on 100 parts by weight of the total amount of the amine polymer and the unsaturation introducing monomer. When the amount of the matrix forming ethylenically unsaturated monomer is less than 10 parts by weight, the interface of the resulting particle becomes unstable and stability of the particle is deteriorated. When the amount exceeds 99,000 parts by weight, copolymerizability of the matrix forming ethylenically unsaturated monomer with the ethylenically unsaturated amine polymer is extremely lowered and the amount of the amino group on the surface of the microparticle becomes too small, which results in deterioration of carrying property of the microparticle.

As described above, an organic polymer microparticle can be obtained by copolymerizing an amine polymer with the matrix forming ethylenically unsaturated monomer, which is dispersed in an solvent, optionally using in combination with a polymerization initiating catalyst, after or during partially modifying the amine polymer with the saturation introducing monomer having at least one functional group which is reactive with a primary amino group in one molecule.

As the solvent used in the present invention, for example, there are water, and aqueous medium such as a mixture of water with high polar solvents (e.g. lower alcohol, tetrahydrofuran, dimethylfolmamide, dioxane, methyl ethyl ketone, etc.). Preferably, water is used.

As described above, in a copolymerization step in the process of the present invention, a microparticle is formed by conducting dispersion/emulsion polymerization in a polar solvent. An emulsifier is absorbed on the surface of the resulting microparticle and remains as an impurity in a drug to be carried and, therefore, it is preferred that no emulsifier is used. However, if necessary, cationic surfactants such as quaternary ammonium salt and nonionic surfactants such as polyoxyalkylene alkyl ether can be used alone or in combination thereof. For the purpose of improving stability of polymerization on synthesis of an organic polymer, a part or all of the amino group may be neutralized with inorganic acids (e.g. hydrochloric acid, phosphoric acid, sulfuric acid, etc.) or organic acids (e.g. acetic acid, etc.).

In the case of using the emulsifier in the polymerization step of the process of the present invention, the amount is preferably 0.1 to 5.0% by weight. When the amount of the emulsifier is less than 0.1% by weight, a good emulsified monomer can not be obtained and, therefore, the particle size of the resulting particle becomes ununiform. When the amount of the emulsifier exceeds 5.0% by weight, it becomes difficult to purify the emulsion and the amount of the emulsifier remaining on the surface of the microparticle is increased.

In the copolymerization step of the present invention, a polymerization initiating catalyst which is known to the art can be optionally used. Examples thereof include organic peroxides (e.g. diacyl peroxide, ketone peroxide, alkyl hydroperoxide, etc.); inorganic peroxides (e.g. hydrogen peroxide, ozone, etc.); oil-soluble azo organic compounds {e.g. azobisvaleronitrile (AIBN, commercially available from Wako Junyaku Co. under the trade name of V-60), 2,2'-azobis(2-methylbutyronitrile) (commercially available from Wako Junyaku Co. under the trade name of V-59), 2,2'-azobis(2,4-dimethylvaleronitrile (commercially available from Wako Junyaku Co. under the trade name of V-65, etc.}; aqueous azo organic compounds {e.g. 2,2'azobis(2-amidinopropane) diacid salt (commercially available from Wako Junyaku Co. under the trade name of V-50), 2,2'-azobis [2-methyl-N-(2-hydroxyethyl)propioneamide (commercially available from Wako Junyaku Co. under the trade name of VA-086), 2,2'-azobis[2-(2-imidazoline-2yl)propane] diacid salt (commercially available from Wako Junyaku Co. under the trade name of VA044), etc} and the like.

In the case of using a polymerization initiator in the polymerization step of the present invention, it is used in an amount enough to initiate polymerization, satisfactorily. The amount is known to the art. In general, the amount is preferably 0.1 to 5.0% by weight.

According to the present invention, by controlling a modification rate of the amino group contained in the amine polymer due to the unsaturation introducing monomer, it is possible to adjust the average particle size of the resulting microparticle in the range of 0.02 to 10.00 μm, optionally. Further, the microparticle of which particle size is adjusted exhibits comparatively narrow distribution of particle size.

It is considered that, when the rate of ethylenic double bond to be introduced into the amine polymer is increased, a point to be copolymerized with the matrix forming ethylenically unsaturated monomer is increased and, therefore, the polymerization reaction proceeds rapidly, which results in decrease of the particle size. On the contrary, when the point to be copolymerized is decreased, the polymerization reaction proceeds slowly and, therefore, growth of the particle due to monomer absorption is liable to be arisen, which results in increase of the particle size. Further, it is considered that the amine polymer functions as a stabilizer of particle interface to contribute to uniformity of the particle size. In Polymer Preprints, Japan, Vol. 40, No. 8, pages 2603–2605, 1991, there is disclosed that a monodisperse polymethyl methacrylate resin particle is synthesized using a macromonomer.

As described above, according to the present invention, there is provided an organic polymer microparticle having an average particle size of about no more than 10μ, which can be suitably used for the application such as diagnostic drugs, pharmaceutical carriers, chromatographic carriers, viscosity modifiers, resin molding materials, paint additives, crosslinking agents, curing agents and cosmetic additives.

The following Examples and Comparative Examples further illustrate the present invention in detail but are not to be construed to limit the scope thereof. In the Examples and Comparative Examples, "parts" and "%s'" are by weight unless otherwise stated.

Preparation Example 1

200 Parts of a 25% aqueous ε-polylysine solution (manufactured by Chisso Co.) obtained biologically and 15.7 parts of glycidyl methacrylate (hereinafter referred to as "GMA") were continuously stirred in a three neck distillation flask at a reaction temperature of 30° C. for 3 hours to obtain a transparent tan aqueous solution.

Preparation Example 2

To a 1 liter three neck distillation flask, 100 parts of 50% ε-polylysine powder (manufactured by Chisso Co.) produced biologically, 15.1 parts of GMA and 900 parts of deionized water were charged, and a mixture was continuously stirred at a reaction temperature of 30° C. for 3 hours to obtain a transparent tan aqueous solution.

Preparation Example 3

To a 300 ml three neck distillation flask, 76.6 parts of a 25% aqueous ε-polylysine solution (manufactured by Chisso Co.) produced biologically, 6.0 parts of GMA, 25 parts of a 10% aqueous acetic acid solution and 100 parts of deionized water, and a mixture was stirred at 30° C. for about one hour to obtain a transparent tan aqueous solution.

Preparation Example 4

To a 100 ml three neck distillation flask, 50 parts of 100% ε-polylysine powder (obtained by freeze drying/pulverizing an aqueous solution), 12 parts of allylglycidyl ether (hereinafter referred to as "AGA"), 35 parts of epoxy resin Cardula E10 (manufactured by Shell Co.) and 180 parts of methanol, and a mixture was reacted at 75°±2° C. for 6 hours to recover about 142 parts of a high viscous polymer. A nonvolatile content was measured (105° C.×3 hours). It was 66.0%.

Preparation Example 5

100 Parts of a 25% aqueous ε-polylysine solution and 6.68 parts of AGA were reacted in a flask at 30° C. for 3 hours to obtain a transparent tan aqueous solution.

Preparation Example 6

100 Parts of 50% ε-polylysine powder, 23 parts of alicyclic epoxy methacrylate (Cyclomer M-100, manufactured by Daicel Chemical Industries Co.) and 200 parts of dioxane were reacted in a flask equipped with a stirrer and a condenser at 40° C. for 3 hours to obtain a slurry-like light tan reaction product.

Preparation Example 7

50 Parts of 100% ε-polylysine powder, 11.5 parts of maleic anhydride and 100 parts of ethanol were reacted in a flask equipped with a stirrer and a condenser at 40° C. for 3 hours to obtain a slurry-like light tan reaction product.

Preparation Example 8

100 Parts of amine-modified silicone oil (KF393, manufactured by Shinetsu Kagaku Kogyo Co.), 16.3 parts of Cyclomer M-100 and 116 parts of isopropyl alcohol (hereinafter referred to as "IPA") were reacted in a flask equipped with a stirrer and a condenser at 30° C. for 5 hours to obtain a viscous liquid.

Preparation Example 9

100 Parts of amine-modified silicone oil (BX16-895, manufactured by Toray Dow Corning Silicone Co.), 17 parts of GMA and 117 parts of IPA were reacted in a flask equipped with a stirrer and a condenser at 50° C. for 2 hours to obtain a viscous liquid.

Preparation Example 10

100 Parts of a 20% aqueous polyallylamine solution (PAA-L, manufactured by Nitto Boseki Co.), 9.96 parts of GMA and 42 parts of a 10% aqueous acetic acid solution were reacted in a flask at 30° C. for 3 hours to obtain a light tan aqueous solution.

Preparation Example 11

100 Parts of a polyallylamine acetate (PAA AcOH, manufactured by Nitto Boseki Co.), 33.2 parts of GMA and 410 parts of water were reacted in a flask at 30° C. for 3 hours to obtain a light tan aqueous solution.

Preparation Example 12

200 Parts of PAA-L and 33.2 parts of GMA were reacted in a flask at 30° C. for 3 hours to obtain a light tan aqueous solution.

Example 1

100 Parts of an aqueous solution obtained in Preparation Example 2, 3.5 parts of methyl methacrylate (hereinafter referred to as "MMA") and 0.1 parts of V-50 (manufactured by Wako Junyaku Co.) which is a water-soluble azo initiating catalyst were charged in a 200 ml three neck distillation flask, and a mixture was reacted at a reaction temperature of 70°±2° C. for 2 hours to obtain a transparent tan emulsion. A particle size of the emulsion was measured by a laser light-scattering method. It was 29±3 nm. Further, the emulsion microparticle was dried with heating to obtain a high hardness coating which exhibits a pencil hardness of 4H. Further, the emulsion was dry-powdered by subjecting it to ultrafiltration followed by spray drying. A total amine value and a tertiary amine value of the dried particle were separately measured by an acetylation method. A primary (and secondary) amine value (hereinafter referred to as an "amine value") obtained from the remainder between the total amine value and the tertiary amine value was 332 mmoles/100 g of dry particle.

Example 2

To a 1 liter separable flask, 76.6 parts of a 25% aqueous ε-polylysine solution (manufactured by Chisso Co.), 2.42 parts of GM, 177.6 parts of MMA, 0.90 parts of V-50 and 544 parts of deionized water were charged, and a mixture was polymerized with continuously stirring at a reaction temperature of 60°±2° C. for 3 hours under nitrogen gas current to obtain an opaque white emulsion. A particle size of the emulsion was measured by a laser light-scattering method. It was 453±43 nm. An amine value was measured according to the same manner as that of Example 1. It was 61.5 mmoles/100 g of particle.

Example 3

To a 1 liter separable flask, 182 parts of an aqueous solution obtained in Preparation Example 3, 173.98 parts of MMA, 0.9 parts of V-50 and 444 parts of deionized water were charged, and a mixture was polymerized with continuously stirring at a reaction temperature of 60°±2° C. for 3 hours under nitrogen gas current to obtain an opaque white emulsion. A particle size of the emulsion was measured by a laser light-scattering method. It was 537±48 nm. The emulsion thus obtained was stable for not less than 6 months under the condition of room temperature. An amine value was measured according to the same manner as that described in Example 1. It was 78 mmoles/100 g of particle.

Example 4

To a 1 liter separable flask, 109 parts of an aqueous solution obtained in Preparation Example 1, 90 parts of styrene, 0.45 parts of V-50 and 420 parts of deionized water were charged, and a mixture was polymerized with continuously stirring at a reaction temperature of 75°±2° C. for 3 hours under nitrogen gas current to obtain an opaque white emulsion. A particle size of the emulsion was measured by a laser light-scattering method. It was 274±31 nm. The emulsion thus obtained was stable for not less than 6 months under the condition of room temperature. An amine value was measured according to the same manner as that described in Example 1. It was 126 mmoles/100 g of particle.

Example 5

To a 1 liter separable flask, 36.3 parts of a 25% aqueous ε-polylysine solution (manufactured by Chisso Co.), 3.02 parts of GMA, 187 parts of MMA, 1.0 parts of V-50 and 772 parts of deionized water were charged, and a mixture was polymerized with continuously stirring at a reaction temperature of 60°±2° C. for 4 hours under nitrogen gas current to obtain an opaque white emulsion. A particle size of the emulsion was measured by a laser light-scattering method. It was 1890±154 nm. A microparticle solid in the emulsion was precipitated within 96 hours. After rinsing was repeated, the precipitated solid was dried in an oven maintained at 50° C. for three days and nights to obtain a white powder having excellent fluidity. An amine value was measured according to the same manner as that described in Example 1. It was 31 mmoles/100 g of particle.

Example 6

9 Parts of a methanol solution obtained in Preparation Example 4, 20 parts of n-butyl acrylate, 60 parts of styrene, 20 parts of ethylhexyl methacrylate, 400 parts of deionized water and 1.0 part of an oil-soluble azo initiating catalyst (manufactured by Wako Junyaku Co.) were mixed with stirring (10,000 rpm/10 minutes) by a high-speed homomixer. Then, a mixture was charged in a 1 liter separable flask and polymerized with continuously stirring (20 rpm) at 60°±2° C. for 3 hours under nitrogen gas current to obtain an opaque white emulsion together with a small amount of an agglomerate. A particle size of the emulsion was measured by a laser light-scattering method. It was 2480±223 nm. An amine value was measured according to the same manner as that described in Example 1. It was 19 mmoles/100 g of particle.

Example 7

50 Parts of an aqueous solution obtained in Preparation Example 5, 133.65 parts of MMA, 12 parts of a 10% aqueous acetic acid solution, 0.7 parts of a cationic azo initiating catalyst VA-044 (manufactured by Wako Junyaku Co.) and 840 parts of water were charged in a flask equipped with a condenser and a stirrer, and a mixture was reacted at 70 for 5 hours under nitrogen gas current. As a result, an emulsion having an average particle size of 254±31 nm was obtained. An amine value was measured according to the same manner as that described in Example 1. It was 65 mmoles/100 g of particle.

Example 8

30 Parts of a dioxane solution obtained in Preparation Example 6, 4.7 parts of a 10% aqueous acetic acid solution, 93 parts of MMA and 680 parts of water were charged in a flask equipped with a condenser and a stirrer. Then, a mixture was heated to 70° C. under nitrogen gas current and 0.5 parts of V-50 and 200 parts of water in a dropping funnel were added dropwise over one hour. Further, it was aged for 4 hours to obtain an emulsion having an average particle size of 365±38 nm. An amine value was measured according to the same manner as that described in Example 1. It was 34 mmoles/100 g of particle.

Example 9

6.7 Parts of an ethanol solution obtained in Preparation Example 7, 98.5 parts of MMA and 700 parts of water were charged in the same flask as that of Example 8. Then, a mixture was heated to 70° C. under nitrogen gas current and 0.5 parts of V-50 and 200 parts of water in a dropping funnel were added dropwise over one hour. Further, it was aged for 2 hours to obtain an emulsion having an average particle size of 674±59 nm. An amine value was measured according to the same manner as that described in Example 1. It was 7 mmoles/100 g of particle.

Example 10

20 Parts of a IPA solution obtained in Preparation Example 8, 23 parts of a 10% aqueous acetic acid solution, 90 parts of MMA, 0.4 parts of V-50 and 900 parts of water were reacted at 70° C. for 3 hours according to the same manner as that described in Example 7 to obtain a slightly transparent emulsion having an average particle size of 63±12 nm. An amine value was measured according to the same manner as that described in Example 1. It was 12 mmoles/100 g of particle.

Example 11

45 Parts of a IPA solution obtained in Preparation Example 9, 46 parts of a 10% aqueous acetic acid solution, 76 parts of MMA, 4 parts of ethylene glycol methacrylate, 0.45 parts of VA-044 and 900 parts of water were reacted at 60° C. for 4 hours according to the same manner as that described in Example 7 to obtain an emulsion having an average particle size of 98±11 nm. An amine value was measured according to the same manner as that described in Example 1. It was 48 mmoles/100 g of particle.

Example 12

100 Parts of an aqueous solution obtained in Preparation Example 10, 60 parts of MMA and 150 parts of water were charged in the same flask as that of Example 8. Then, a mixture was heated to 60° C. under nitrogen gas current and 0.3 parts of VA-044 and 100 parts of water in a dropping funnel were added dropwise over one hour. Further, it was aged for 3 hours to obtain an emulsion having an average particle size of 125±21 nm. An amine value was measured according to the same manner as that described in Example 1. It was 224 mmoles/100 g of particle.

Example 13

23 Parts of an aqueous solution obtained in Preparation Example 11, 95 parts of MMA and 680 parts of water were charged in the same flask as that of Example 8. Then, a mixture was heated to 60° C. under nitrogen gas current and 0.5 parts of V-50 and 200 parts of water in a dropping funnel were added dropwise over one hour. Further, it was aged for 3 hours to obtain an emulsion having an average particle size of 215±24 nm. An amine value was measured according to the same manner as that described in Example 1. It was 42 mmoles/100 g of particle.

Example 14

116 Parts of an aqueous solution obtained in Preparation Example 12, 3.4 parts MMA, 0.2 parts of V-50 and 345 parts of water were reacted at 60° C. for 4 hours according to the same manner as that described in Example 7 to obtain a slightly transparent emulsion having an average particle size of 48±6 nm. An amine value was measured according to the same manner as that described in Example 1. It was 683 mmoles/100 g of particle.

Example 15

10 Parts of high purity chitosan (chitosan 100L, manufactured by Wako Junyaku Co.), 29.8 parts of a 10% aqueous acetic acid solution, 1.8 parts of GMA and 88 parts of water were reacted in a flask at 30° C. for 3 hours and 85 parts of MMA and 690 parts of water were added. Then, a mixture was heated to 60° C. under nitrogen gas current and 0.5 parts of V-50 and 200 parts of water in a dropping funnel were added dropwise over one hour. Further, it was aged for 3 hours to obtain an emulsion having an average particle size of 648±86 nm. An amine value was measured according to the same manner as that described in Example 1. It was 31 mmoles/100 g of particle.

Comparative Example 1

40 Parts of a 25% aqueous ε-polylysine solution, 90 parts of MMA and 660 parts of water were charged in a 1 liter flask equipped with a condenser and a stirrer. Then a mixture was heated to 70° C. and 1.0 part of V-50 and 200 parts of water in a dropping funnel were added dropwise over one hour. Twenty minutes after the beginning of dropping, the polymerization began to take place, but a polymer component was rapidly agglomerated/precipitated with the proceeding polymerization and, therefore, the polymerization was terminated.

Comapartive Example 2

100 Parts of PAA-10C (10% aqueous solution of polyallylamine, manufactured by Nitto Boseki Co.), 90 parts of MMA and 610 parts of water were charged in the same flask as that of Comparative Example 1. Then, a mixture was heated to 60° C. and 1.0 parts of V-50 and 200 parts of water were added dropwise over one hour. Large agglomeration of the polymer component bagan to take place immediately after the beginning of the polymerization. Thereafter, it was aged for 5 hours to obtain a cloudy emulsion. A particle size of the emulsion was measured by a laser light-scattering method. It showed wide particle size distribution (589±178 nm).

Example 16

According to the same manner as that described in Preparation Example 1 except that an amount of GMA to be added was appropriately varied, ethylenically unsaturated amine polymers having various modification rate of amino group due to GMA (10, 25, 50, 75 and 99 mole %) were prepared.

According to the same manner as that described in Example 2, 150 parts of each ethylenically unsaturated amine polymer solution of which concentration was adjusted to 10% by diluting with deionized water, 135 parts of MMA, 0.8 parts of V-50 and 465 parts of deionized water were polymerized in a 1 liter separable flask. An opaque or cloudy emulsion was obtained, respectively.

An average particle size of the microparticles obtained by using amine polymers having various GMA modification rate was measured, respectively. The results are shown in Table 1 below.

TABLE 1

| GMA modification rate of amine polymer (mole %) | Average particle size of microparticle (nm) |
|---|---|
| 10 | 439 ± 47 |
| 25 | 315 ± 34 |
| 50 | 225 ± 27 |
| 75 | 97 ± 14 |
| 99 | 54 ± 21 |

As described above, it was shown that the average particle size of the microparticle decreases as GMA modification rate of amine polymer increases.

What is claimed is:

1. An organic polymer microparticle which is obtained by copolymerizing in an aqueous medium;
   (a) an ethylenically unsaturated amine polymer having an ethylenic double bond, obtained by reacting an amine polymer having at least two primary amino groups, selected from the group consisting of polyamino acids, polyamine-vinyl polymers and mixtures thereof, with 0.01 to 0.99 molar equivalents based on the amount of the primary amino groups, of an unsaturation introducing monomer having at least one functional group which is reactive with the primary amino group and an ethylenic double bond, selected from the group consisting of glycidyl group-containing monomers, with
   (b) a matrix forming ethylenically unsaturated monomer selected from the group consisting of aromatic vinyl monomers, alkyl methacrylates, methacrylamides, methacrylonitriles and mixtures thereof; an amount of the matrix forming ethylenically unsaturated monomer being 10 to 99,000 parts by weight based on 100 parts by weight of the total amount of said amine polymer and said unsaturation introducing monomer.

2. A process for producing an organic polymer microparticle comprising:
   (i) a step of reacting an amine polymer having at least two primary amino groups with 0.01 to 0.99 molar equivalents based on the amount of the primary amino group, of an unsaturation introducing monomer having at least one functional group which is reactive with the primary amino group and an ethylenic double bond to obtain a reaction mixture containing an ethylenically unsaturated amine polymer having an ethylenic double bond, and
   (ii) a step of formulating 10 to 99000 parts by weight based on 100 parts by weight of the total amount of the amine polymer and the unsaturation introducing monomer, of a matrix forming ethylenically unsaturated monomer in the reaction mixture to copolymerize the ethylenically unsaturated amine polymer with the matrix forming ethylenically unsaturated monomer in an aqueous medium.

3. The process according to claim 1 wherein reaction is conducted by dispersion or emulsion polymerization.

4. The process according to claim 1 wherein said amine polymer is neutralized with an inorganic acid.

5. The process according to claim 2 wherein polymerization is initiated by a polymerization initiator.

* * * * *